United States Patent [19]

Nobuta

[11] Patent Number: 4,735,410
[45] Date of Patent: Apr. 5, 1988

[54] ROWING MACHINE

[75] Inventor: Yoshiji Nobuta, Nara, Japan

[73] Assignee: Mizuno Corporation, Osaka, Japan

[21] Appl. No.: 84,981

[22] Filed: Aug. 12, 1987

[30] Foreign Application Priority Data

Aug. 13, 1986 [JP] Japan ................... 61-191133

[51] Int. Cl.$^4$ .............. A63B 21/00; A63B 21/24
[52] U.S. Cl. .................... 272/72; 272/130;
 272/129; 272/DIG. 5; 272/DIG. 6
[58] Field of Search ............ 272/69, 72, 73, 129,
 272/130, DIG. 5, DIG. 6

[56] References Cited

U.S. PATENT DOCUMENTS

| | | | |
|---|---|---|---|
| 3,675,640 | 7/1972 | Gatts | 272/69 |
| 3,869,121 | 3/1975 | Flavell | 272/DIG. 6 |
| 4,167,019 | 9/1979 | Shepperd | 358/22 |
| 4,278,095 | 7/1981 | Lapeyre | 272/69 |
| 4,408,613 | 10/1983 | Relyea | 272/DIG. 5 |
| 4,647,741 | 6/1987 | Pasierb, Jr. et al. | |

FOREIGN PATENT DOCUMENTS 184108 8/1986 Japan.

Primary Examiner—Richard J. Apley
Assistant Examiner—S. R. Crow
Attorney, Agent, or Firm—W. G. Fasse; D. H. Kane, Jr.

[57] ABSTRACT

The inventive rowing machine detects angular velocity of a pair of oars pulled by an exerciser to move a moving image appearing on a CRT display on the basis of the detection output while controlling the display to change the direction of movement of the moving image in response to pulling of one of the pair of oars when the moving image on the CRT display threatens to run against an obstacle image. Further, physiological condition of the exerciser is detected by the physiological condition detector to reduce the resistance force against rotation of the pair of oars by loading device in response to detection of small reserve strength of the exerciser with respect to the loading device, and to increase the resistance force against rotation of the pair of oars by loading device in respone to detection of large reserve strength of the exerciser with respect to the loading device.

11 Claims, 7 Drawing Sheets (a)

ROWING MACHINE

BACKGROUND OF THE INVENTION

1. Field of the Invention

The present invention relates to a rowing machine. More specifically, it relates to a rowing machine through which an exerciser can enjoy a video game while taking indoor exercise by pulling a pair of oars.

2. Description of the Prior Art

In general, a rowing machine is fixed on an indoor floor so that an exerciser is seated on the same to pull a pair of oars which are applied with resistance, thereby to improve his cardiopneumatic function and muscular strength through exercise for applying a load on his arms and legs. Such exercise must be continued over a prescribed time in order to improve the cardiopneumatic function through the rowing machine. This time is measured from effectuation of aerobic energy trap function of muscles, and hence it is believed that at least 12 minutes are required for the exercise.

However, such exercise through the rowing machine is extremely monotonous. Thus, it is burdensome for the exerciser to perform monotonous exercise for a long time while applying a load on his body, and hence the exerciser tends to give up the exercise in a short time, whereby his cardiopneumatic function cannot be sufficiently improved.

There has been proposed an invention relating to a rowing machine which is provided with a picture image display apparatus so that the user can positively take exercise in U.S. patent application No. 762,709 filed on Aug. 5, 1985. In this prior art, a CRT display is provided in front of the rowing machine to display moving picture images when the user pulls oars of the rowing machine. However, the user cannot take appropriate exercise in response to his physical strength through such a rowing machine provided with a picture image display apparatus.

SUMMARY OF THE INVENTION

Accordingly, the principal object of the present invention is to provide a rowing machine, through which the user can positively take exercise with interest while being relieved of a burden originating in monotonous exercise and the user can take appropriate exercise in response to his physical strength.

Briefly stated, a moving image corresponding to the rowing machine and an image for influencing the moving image are displayed on display means. The exerciser is seated on a seat slidably mounted on a frame to pull a pair of oars while viewing the display on the display means. The pair of oars are provided with angular velocity detecting means for detecting angular velocity thereof, so that relative display positions of the moving image and the influencing image are sequentially changed in response to the angular velocity detected when the exerciser pulls the pair of oars. When the exerciser pulls one of the pair of oars, the moving image is moved to the left or the right in response to the current angular velocity. Further, physiological condition of the exerciser is detected to reduce the resistance force against rotation of the pair of oars by load means in response to detection of small reserve strength of the exerciser with respect to the load means.

Thus, according to the present invention, the relative display positions of the moving image and the influencing image appearing on the display means are sequentially changed when the exerciser pulls the pair of oars, whereby the exerciser can enjoy exercise by viewing the display on the display means, to be relieved of a burden originating in monotonous exercise and the exerciser can take optimum exercise.

In a preferred embodiment of the present invention, displayed on display means are a moving image and an image of a water current serving as a path for the moving image as well as images of obstacles, to increase resistance force against rotation of a pair of oars in response to display of a swift water current image or a head wind image while reducing resistance force against the pair of oars provided by loads in response to display of a slow current image or a tail wind image.

These and other objects, features, aspects and advantages of the present invention will become more apparent from the following detailed description of the present invention when taken in conjunction with the accompanying drawings.

BRIEF DESCRIPTION OF THE DRAWINGS

FIG. 4a is a sectional view of a support member as shown in FIG. 1;

FIG. 4b is a front view of the dividing plate shown in FIG. 4a.

DESCRIPTION OF THE PREFERRED EMBODIMENTS

Figure 1:
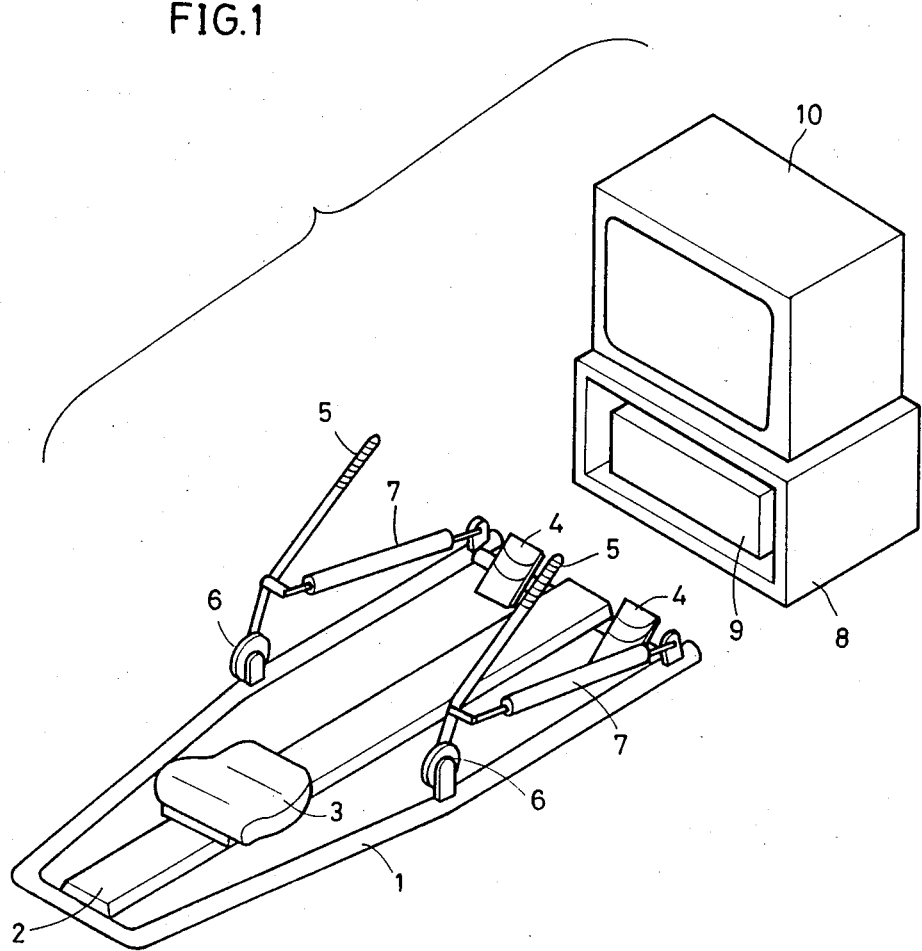
FIG. 1 is a sketch drawing showing an embodiment of the present invention.

FIG. 1 is a sketch drawing showing an embodiment of the present invention.

Referring to FIG. 1, description is now made on the structure of this embodiment. A frame 1 is formed by bending a pipe and a sliding plate 2 is mounted on the longitudinal center of the frame 1 while a seat 3 is slidably provided on the sliding plate 2. A pair of footboards 4 are mounted on the front portion of the frame 1. A pair of oars 5 are rotatably provided on the frame 1 through support members 6 on both sides of the seat 3. Cylinders 7 for serving as loads are provided between the pair of oars 5 and the front portion of the frame 1, to apply resistance against rotation of the oars 5. A rack 8 is arranged in front of the rowing machine to contain a computer 9, while a CRT display 10 is provided on the rack 8. In the rowing machine of such structure, an exerciser is seated on the seat 3 and puts his feet on the footboards 4, to take exercise by pulling the oars 5 while viewing the screen of the CRT display 10.

Figure 2:
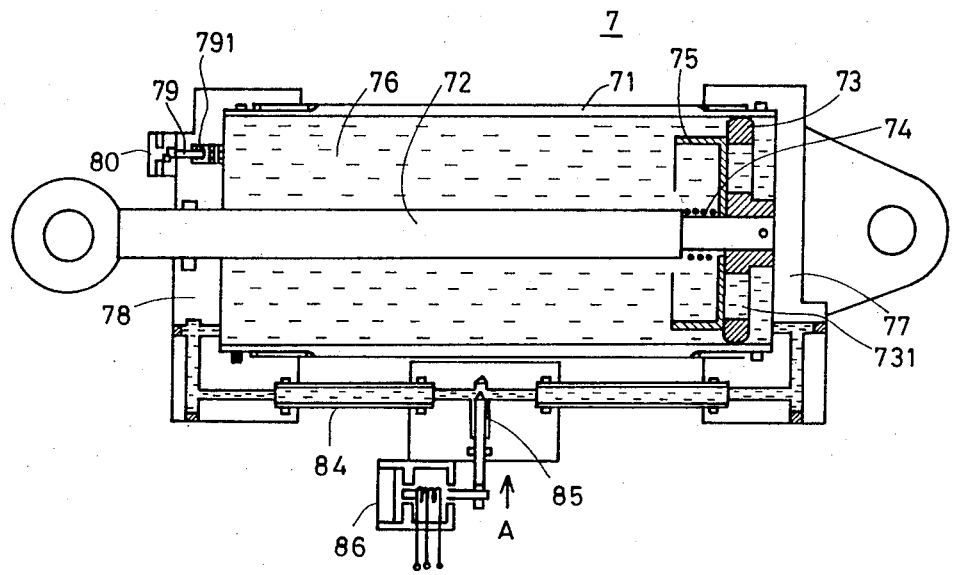
FIG. 2 is a sectional view of a cylinder as shown in FIG. 1.
Figure 3:
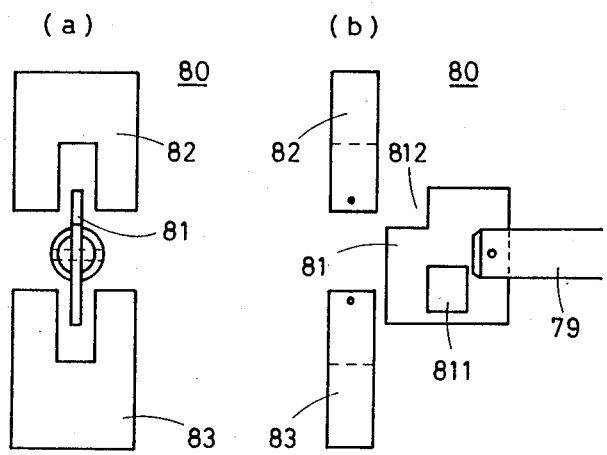
FIG. 3a is an enlarged front view of an encoder as shown in FIG. 2.
FIG. 3b is an enlarged side view of an encoder as shown in FIG. 1.

FIG. 2 is a sectional view of each cylinder as shown in FIG. 1, and FIG. 3 illustrates the structure of an encoder as shown in FIG. 1.

Referring to FIGS. 2 and 3, description is now made on the structure of the cylinder serving as a load. Each cylinder 7 includes a cylinder tube 71, which receives a piston rod 72. A subpiston 75 is mounted on one end of the piston rod 72 through a coil spring 74, while a piston 73 is mounted on the front end portion of the subpiston 75. The piston 73 is provided with a plurality of holes 731. Oil 76 is filled in the cylinder tube 71, while an end of the cylinder tube 71 is covered by a head cover 77 and the other end is covered by a rod cover 78. The other end of the piston rod 72 is mounted on the corresponding oar 5 as shown in FIG. 1.

A bypass path 84 communicates with the head cover 77 and the rod cover 78 so that the oil 76 bypasses the cylinder tube 71, and a needle valve 85 is provided in an intermediate portion of the bypass path 84. This needle valve 85 is adapted to regulate the flow rate of the oil 76 flowing in the bypass path 84, thereby to adjust the resistance against rotation of the oar 5. Thus, the needle valve 85 is driven by a torque motor 86.

When the exerciser pulls the oar 5 toward this side in a closed state of the needle valve 86, the piston rod 72 is pulled toward the other side (left-hand side in FIG. 2) so that the subpiston 75 and the piston 73 are also moved toward the other side to compress the oil 76. Thus, when the oar 5 is pulled toward this side, resistance is applied by compression of the oil 76. When pressure is applied by the subpiston 75 and the piston 73, the oil 76 flows toward this side (right-hand side in FIG. 2) through a small clearance defined between the piston 73 and the inner wall of the cylinder tube 71.

When the oar 5 is thus pulled toward this side and then returned to its original position, the subpiston 75 is subjected to pressure by the oil 76 through the holes 731 of the piston 73, and the pressurized oil 76 presses the subpiston 75 to the other side against elastic force of the coil spring 74. Thus, a clearance is defined between the subpiston 75 and the piston 73, so that the oil 76 flows to the other side through the clearance. In other words, resistance is applied to rotation of the oar 5 by pressure of the oil 76 when the oar 5 is pulled toward this side, while no such pressure is applied by the oil 76 when the oar 5 is returned to its original position.

When the torque motor 86 is driven to move the needle valve 85 along an arrow A, most of the oil 76 pressurized by the piston 73 and the subpiston 75 through the oar 5 pulled toward this side again flows into the cylinder tube 71 from the head cover 77 through the rod cover 78 and the bypass path 84, thereby to reduce resistance force in pulling of the oar 5. Thus, the resistance force against the oar 5 can be varied depending on the degree of closure of the bypass path 84 by the needle valve 8.

An encoder 80 is provided in the vicinity of the rod cover 78, in order to detect the pressure of the oil 76 in the cylinder tube 71. The rod cover 78 is provided with a piston 79 which operates in response to the pressure applied to the oil 76, and an encode plate 81 is mounted on the forward end of the piston 79, as shown at (a) and (b) in FIG. 3. This encode plate 81 is provided with a rectangular hole 811, while the same is notched in a corner part 812 in its forward end portion. A pair of photointerrupters 82 and 83 are provided in front of the encode plate 81 along the direction of movement thereof.

By virtue of such structure of the encoder 80, the photointerrupters 82 and 83 detect light emitted when the piston 73 is at least close to the right hand side in FIG. 2 and the oil pressure is low, to output signals of "0" and "0". When the piston rod 72 is pulled to the left hand side in FIG. 2 so that the piston rod 73 pressurizes the oil 76, the piston 79 mounted on the rod cover 78 is also pressed against the elastic force of the coil spring 791 and the encode plate 81 provided on its forward end portion is moved toward the photointerrupters 82 and 83. When the oil pressure is low, the photointerrupter 83 is shielded against the light by the encode plate 81 while the photointerrupter 82 detects the light passing through the notched part 812 of the encode plate 81. Thus, the photointerrupters 82 and 83 output signals of "0" and "1" respectively. When the oil pressure is higher, the photointerrupter 82 is shielded against the light by the encode plate 81 while the photointerrupter 83 detects the light passing through the hole 811 provided in the encode plate 81. Thus, the photointerrupters 82 and 83 output signals of "1" and "0" respectively. When the oil pressure further becomes higher, both of the photointerrupters 82 and 83 are shielded against the light by the encode plate 81, to output signals of "1" and "1".

Figure 4:
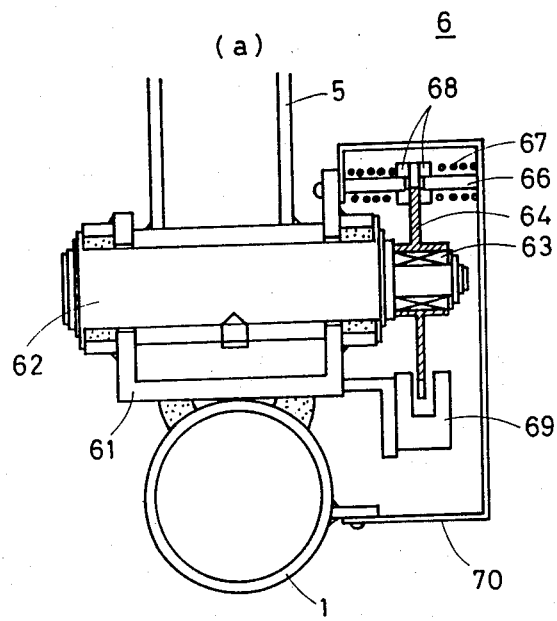
Figure 4:
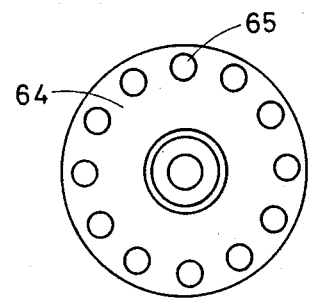

FIG. 4 is a sectional view of each support member as shown in FIG. 1.

The support member 6 contains means for detecting the angular velocity in rotation of the oar 5 in place of the encoder 80 as shown in FIG. 3. A bracket 61 is mounted on the frame 1 to support a rotary shaft 62, to which a lower end of the oar 5 is fixed. A dividing plate 64 is mounted on the rotary shaft 62 through a one way clutch 63. The one way clutch 63 is adapted to rotate the dividing plate 64 when the oar 5 is pulled toward this side while inhibiting rotation of the dividing plate 64 when the oar 5 is returned to its original position. As shown at (b) in FIG. 4, the dividing plate 64 is provided with a plurality of holes 65 along its peripheral edge. A photointerrupter 69 is mounted on the bracket 61 in relation to the dividing plate 64. The photointerrupter 69 is adapted to detect the angular velocity in pulling of the oar 5 by detecting light passing through the holes 65 upon rotation of the dividing plate 64.

Further, a brake friction pad 68 is provided in place of the load for applying resistance against the oar 5 by the cylinder 7 as shown in FIG. 2. In order to apply resistance to the dividing plate 64, the brake friction pad 68 is held by a shaft 66 and a spring coil 67 provided between the bracket 61 and the cover 70. The brake friction pad 68 is brought into contact with the dividing plate 64, thereby to apply resistance to rotation of the dividing plate 64. Contact force of the brake friction pad 68 with respect to the dividing plate 64 is increased/decreased by a plunger (not shown), thereby to vary the resistance against the dividing plate 64.

Figure 5:
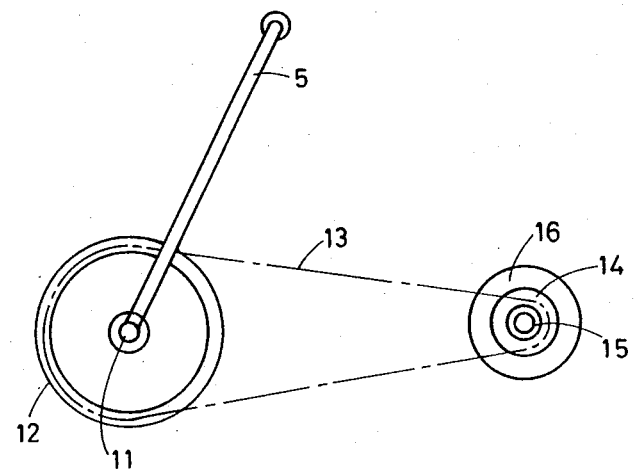
FIG. 5 illustrates another example of a loading device for applying resistance to an oar.

FIG. 5 illustrates another example of a loading device for applying resistance to the oar 5. In the example as shown in FIG. 5, a chain wheel 12 is provided on a rotary shaft 11 of the oar 5 and a chain 13 is extended along the chain wheel 12, so that another chain wheel 14 is rotated by the chain 13 upon pulling of the oar 5. The chain wheel 14 is coaxially provided with a one way clutch 15 and an eddy current load torque generator 16. Resistance against rotation of the oar 5 can be varied by adjusting the current supplied to the eddy current load torque generator 16. The one way clutch 15 is so provided that resistance is applied against rotation of the oar 5 when the same is pulled by the exerciser toward this side while no such resistance is applied when the oar 5 is returned to its original position.

Figure 6:
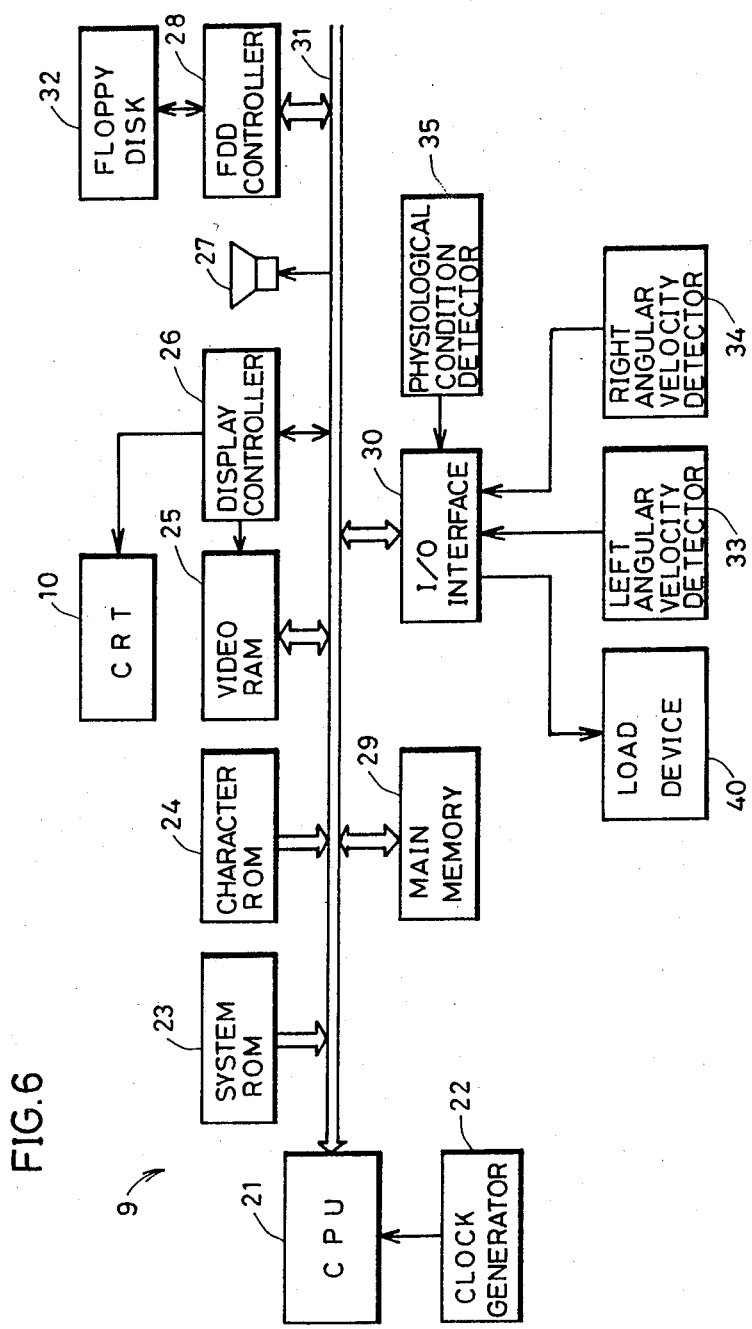
FIG. 6 is a schematic block diagram showing the embodiment of the present invention.

FIG. 6 is a schematic block diagram showing electrical structure of the embodiment of the present invention.

Description is now made on the electrical structure of this embodiment with reference to FIG. 6. The computer 9 includes a CPU 21, which is supplied with a clock signal from a clock generator 22. The CPU 21 is connected with a bus 31, which is connected with a system ROM 23, a character ROM 24, a video RAM 25, a display controller 26, a speaker 27, an FDD controller 28, a main memory 29 and an I/O interface 30.

Figure 7:
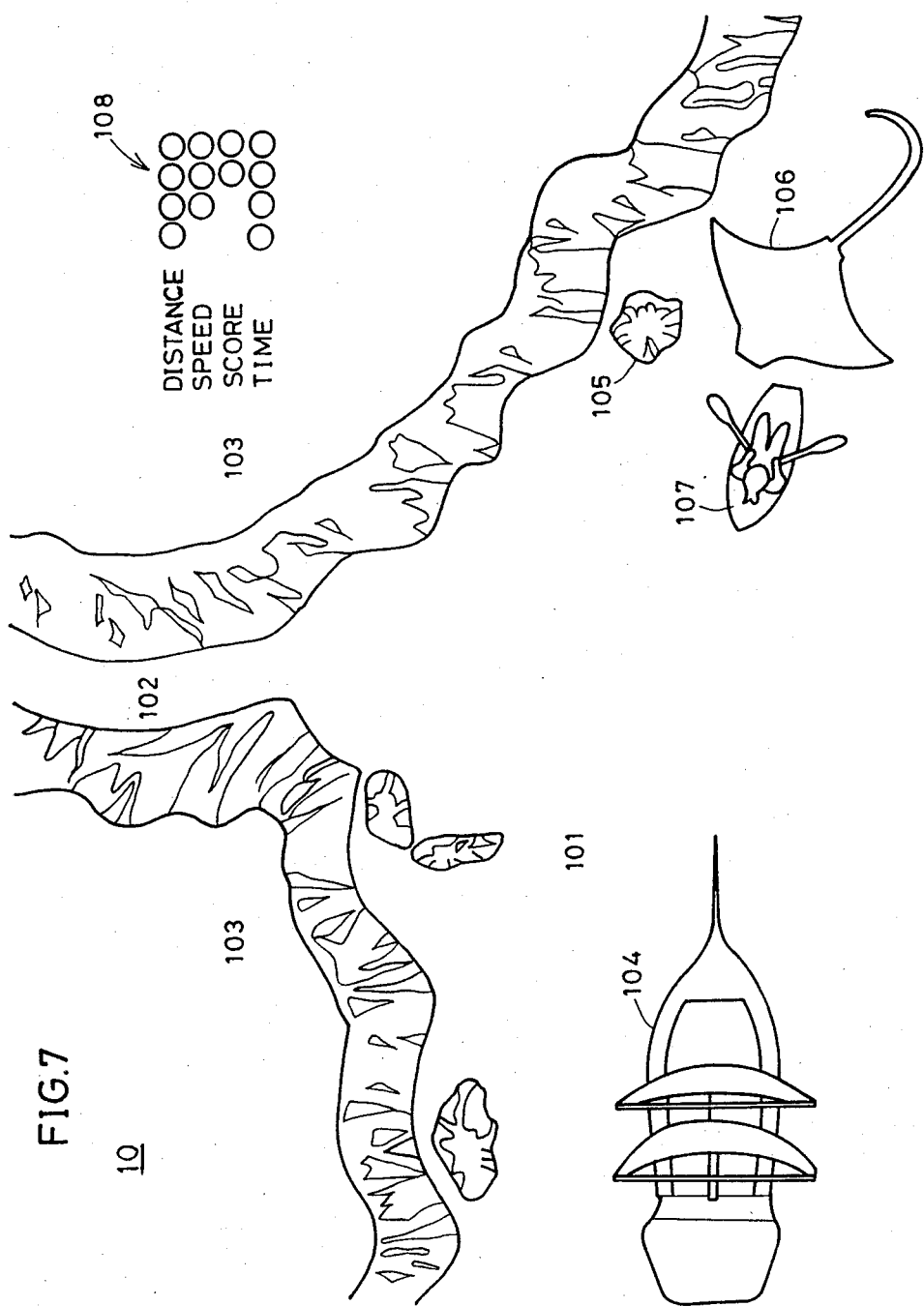
FIG. 7 illustrates examples of images displayed on a CRT display in the embodiment of the present invention.

The system ROM 23 stores programs for executing the entire operation of the computer 9. The character ROM 24 is adapted to generate signals indicating numerical values such as the travel distance and the travel speed and characters appearing on the CRT display 10. The video RAM 25 has storage regions corresponding to display regions of the CRT display 10, to store data of picture images to appear on the CRT display 10. The display controller 26 is adapted to control the image data displayed on the video RAM 25. The speaker 27 generates sounds required for a video game. The FDD controller 28 is adapted to control a floppy disk 32. This floppy disk 32 previously stores programs based on flow charts shown in FIGS. 8 and 9 as hereinafter described, while forming picture signal generating means for generating picture signals for displaying a boat image serving as an example of a moving object, a travel path image for the boat image and obstacle images such as those of a land and a pirate ship as shown in FIG. 7. Such picture signal generating means is not restricted to the floppy disk 32, but may be formed by a ROM or the like.

The main memory 29 stores data operated by the CPU 21, as well as the program read from the floppy disk 32. The I/O interface 30 is connected with a load 40, left and right angular velocity detectors 33 and 34 and physiological condition detector 35. The load 40 is formed by a plunger or the like for making the dividing plate 64 press the brake friction pad 68 as shown in FIG. 4. The left and right angular velocity detectors 33 and 34 are formed by the photointerrupters 82 and 83 as shown in FIG. 2, the photointerrupter 69 as shown in FIG. 4 or the like. The physiological condition detector 35 is adapted to detect the pulse, temperature, amount of perspiration and the like of the exerciser. A pulse sensor is mounted on an earlobe of the exerciser to detect his pulse, while a thermistor thermometer is adapted to detect his temperature and a humidity sensor or the like is employed as a perspiration sensor. In place of the CRT display 10, a liquid crystal display or a plasma display may be employed as display means.

Figure 8:
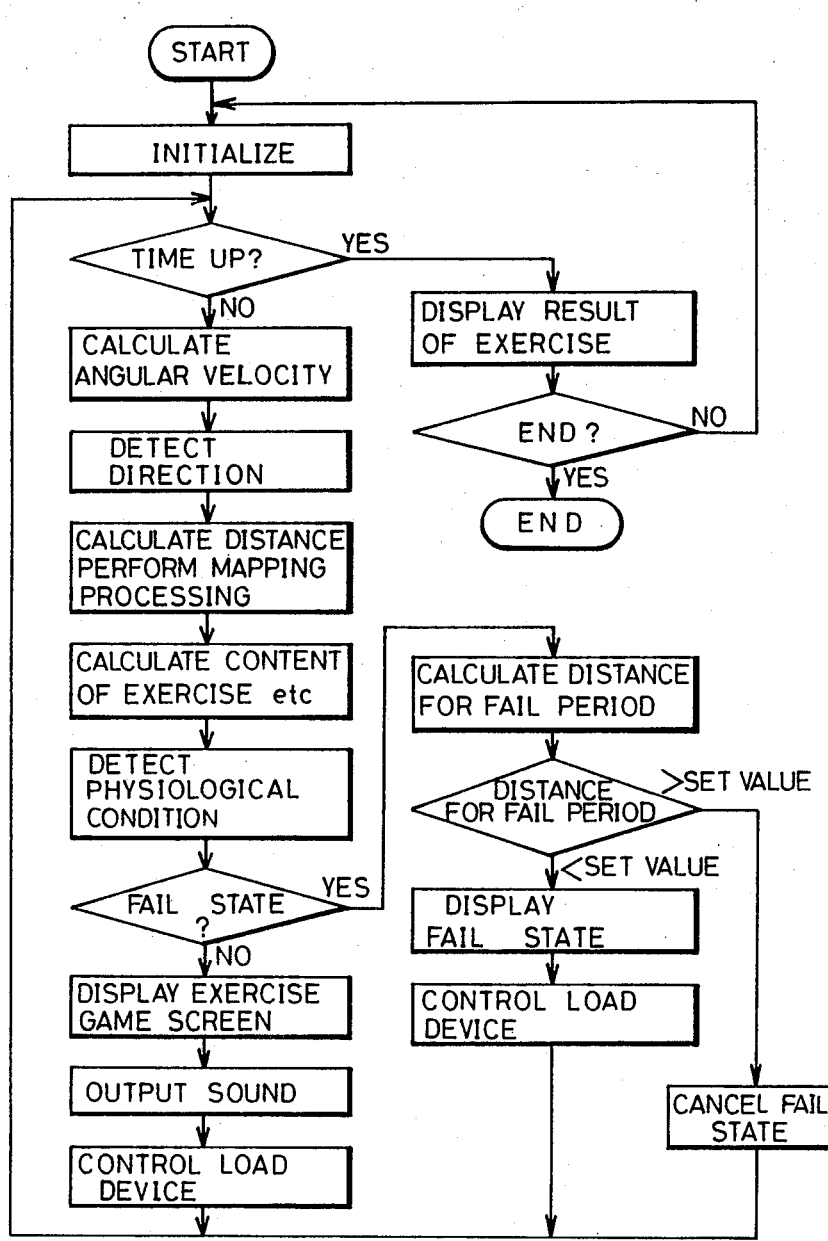
FIG. 8 is a flow chart for illustrating the operation of the embodiment of the present invention.

FIG. 7 illustrates examples of picture images displayed on the CRT display in the embodiment of the present invention, and FIG. 8 is a flow chart for illustrating operation of this embodiment.

With reference to FIGS. 1 to 8, description is now made on the operation of this embodiment. As shown in FIG. 7, the CRT display 10 displays an ocean image 101, a river image 102 and a land image 103 as well as a pirate ship image 104, a rock image 105 and a manta ray image 106 serving as obstacle images. Further, a boat image 107 serving as a moving object is displayed in correspondence to the rowing machine.

When the exerciser is seated on the seat 3 of the rowing machine as shown in FIG. 1 and puts his feet on the footboards 4 to pull the oars 5, the boat image 107 is forwardly moved on the CRT display 10. The pirate ship image 104 and the manta ray image 106 are displayed to offensively approach the boat image 107, and the exerciser pulls both or only one of the oars 5 to avoid the obstacle images, thereby to go upstream the river image 102 from the ocean image 101. The ocean image 101 can be displayed in the form of an ocean current, so that, when the boat image 107 is moved against the ocean current, resistance is applied to rotation of the oars 5 by the load device 40 in response to the ocean current. When the boat image 107 goes upstream the river image 102, resistance against rotation of the oars 5 is increased/decreased by the load device 40 in response to the water current. The ocean image 101 may be displayed choppily by a head wind to increase resistance, while the resistance may be reduced in case of a tail wind.

Further, the load device 40 is controlled in response to the exerciser's reserve strength with respect to the load device 40, so that the exerciser can take optimum exercise.

If the boat image 107 comes into contact with the rock image 105 or the land image 103, the boat image 107 enters a fail state. The boat image 107 may be sunk unless the oars 5 are pulled over a prescribed number of times within a prescribed period.

The boat image 107 is not recovered from the fail state unless the oars 5 are pulled over a prescribed number of times within a prescribed period. When the obstacle images are avoided, points are scored to be displayed on an auxiliary screen 108 of the CRT display 10. The auxiliary screen 108 can display the elapsed time from starting of the exercise, the travel distance, the travel speed and the like.

When power is so applied that the exerciser can play the aforementioned video game while taking exercise, the CPU 21 clears registers etc. contained therein as shown in FIG. 8. Then the CPU 21 reads total program and image data of the screen to appear on the CRT display 10 from the floppy disk 32 through the FDD controller 28, to write the same in the main memory 29 and the video RAM 25. The display controller 26 makes the initial screen appear on the CRT display 10, to perform initialization.

Thereafter the CPU 21 determines whether or not the time is up. This time is set for a minimum period required for improving the cardiopneumatic function of the exerciser, e.g., for 12 minutes. This time is counted by a timer (not shown) contained in the I/O interface 30. This time may be counted in a software manner by a program.

When a determination is made that the time is not up, the CPU 21 performs processing for calculating the angular velocity of each oar. When the exerciser pulls the oars 5, the dividing plate 64 as shown at (a) in FIG. 4 is rotated so that the photointerrupter 69 detects light passing through the hole 65 following the rotation of the dividing plate 64. Detected pulses outputted from the photointerrupter 69 are supplied to a counter (not shown) contained in the I/O interface 30, to be counted by the same. The counter output is supplied to the CPU 21. The CPU subtracts a constant value alpha from the counter value when the boat image 107 goes against the current of the ocean image 101 or a head wind, while adding the constant value alpha to the counter value when the boat image 107 goes along the ocean current or on a tail wind. The CPU 21 calculates the travel speed of the boat image 107 on the display screen on the basis of the increment in the counter value per constant period to determine the travel distance of the boat image 107 on the display screen, thereby to operate distances to the land image 103, the pirate ship image 104, the rock image 105, the manta ray image 106 and the like. When only one of the pair of oars 5 is pulled, the CPU 21 determines the direction in which the boat image 107 is to be moved. The physiological condition detector 35 detects the exerciser's reserve strength with respect to the load device 40.

Then the CPU 21 determines whether or not the computer program is in the fail state. Namely, the CPU 21 determines whether or not the boat image 107 runs into the land image 103, the pirate ship image 104, the rock image 105 or the manta ray image 106. If the determination is no, the CPU 21 displays the screen for the exercise game on the CRT display 10. Namely, the CPU 21 displays the images corresponding to the distances obtained by the aforementioned operation and rightwardly moves the boat image 107 when only the left oar 5 is pulled while leftwardly moving the boat image 107 when only the right oar 5 is pulled. Further, the CPU 21 outputs a sound when the boat image 107 avoids the obstacle image such as the land image 103 or the rock image 105, while controlling the load device 40 when the boat image 107 goes against the ocean current or the head wind, to increase the resistance against rotation of the oars 5.

When the physiological condition detector 35 detects the exerciser's reserve strength with respect to the load device 40, to accelerate the current of the ocean image 101 or the river image 102 appearing on the CRT display 10 or strengthen the head wind and increase the resistance applied to the oars 5 by the load device 40 when the exerciser's pulse rate is moderate for example, while slowing down the current of the ocean image 101 or the river image 102 or strengthening the tail wind and reducing the resistance applied to the oars 5 by the load device 40 when the exerciser's pulse rate is too high. Thus, the load device 40 is controlled in response to the exerciser's reserve strength with respect to the load device 40, so that the exerciser can take optimum exercise.

When the fail state occurs, the boat image 102 is not recovered unless the oars 5 are pulled over a prescribed number of times within a prescribed period. Therefore, the CPU 21 increases the angular velocity of the oars 5 upon pulling by the exerciser, to perform distance calculation for the fail period. Then the CPU 21 determines whether or not the calculated distance is in excess of a predetermined set value, to indicate the fail state if the determination is no. Namely, the CPU 21 makes a mark (not shown) indicating the fail state or the like on the CRT display 10 and controls the load device 40 to change rotational resistance of the oars 5. If the distance for the fail period is in excess of the set value, the CPU 21 cancels the fail state to return the program to the former state.

Although the boat image 107 is displayed on the CRT display 10 as an image corresponding to the rowing machine in the aforementioned embodiment, the present invention is not restricted to such display but the image of a person who walks on the ground may be displayed so that the person runs fast when the exerciser pulls the oars 5 at a high speed.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A rowing machine comprising:
   display means;
   a frame provided in front of said display means;
   a seat slidably mounted on said frame;
   a pair of oars rotatably supported in portions of said frame on both sides of said seat to be pulled by an exerciser seated on said seat;
   angular velocity detecting means provided in correspondence to respective ones of said pair of oars for detecting angular velocity values of respective said oars upon pulling of the same;
   picture signal generating means for generating a moving image signal for displaying a moving image on said display means and a picture signal for displaying an image for influencing movement of said moving image;
   load means for applying resistance against rotation of respective ones of said pair of oars;
   physiological condition detecting means for detecting physiological condition of said exerciser; and
   control means for displaying said moving image and said influencing image on the basis of picture signals generated from said picture signal generating means to control display so that relative display positions of said moving image and said influencing image displayed on said display means are changed in response to relative angular velocity values detected by said respective oar angular velocity detecting means while altering said resistance force provided by said load means against said rotation of respective ones of said pair of oars in response to the physiological condition of said exerciser with respect to said load means by said physiological condition detecting means.

2. A rowing machine in accordance with claim 1, wherein
   said picture signal generating means includes means for generating a travel path image signal for displaying the image of a travel path for said moving image and an obstacle image signal for displaying the image of an obstacle for obstructing movement of said moving image,
   said display means includes means for displaying a travel path image and an obstacle image on said display means on the basis of said travel path image signal and said obstacle image signal generated from said picture signal generating means, and
   said control means includes means for controlling display so that said moving image is moved along said travel path image on the basis of detection output from said angular velocity detecting means and controlling said moving image to be moved to the left or the right in response to detection of angular velocity of one of said pair of oars.

3. A rowing machine in accordance with claim 1, wherein
   said picture signal generating means includes means for generating a signal indicating a water current or the direction of the wind as said travel path image, and
   said control means includes means for increasing resistance force provided by said load means against said rotation of respective ones of said pair of oars in response to generation of a picture signal simulating a swift current or a head wind from said picture signal generating means and reducing said resistance force provided by said load means against said rotation of respective ones of said pair of oars in response to generation of a picture signal simulating a slow current or a tail wind.

4. A rowing machine in accordance with claim 3, wherein
each of said load means includes a cylinder provided between said frame and the corresponding one of said pair of oars for applying resistance to said corresponding one of said oars by a piston driven by hydraulic pressure.

5. A rowing machine in accordance with claim 4, wherein
each of said angular velocity detecting means includes:
a second piston linearly moved by hydraulic pressure following operation of said piston;
encoder means coupled with said second piston; and
optical sensor means for outputting an encode signal responsive to the amount of load on said piston in response to operation of said encoder means.

6. A rowing machine in accordance with claim 3, further comprising support members for rotatably mounting said pair of oars on said frame,
each of said support members including a disc rotated interlockingly with the corresponding one of said oars,
each of said load means including a brake for applying resistance by being in contact with said disc.

7. A rowing machine in accordance with claim 3, further including support members for rotatably mounting said pair of oars on said frame respectively,
each of said support members including a disc rotated interlockingly with the corresponding one of said oars,
each of said load means including eddy current generating means for applying resistance against rotation of said disc by generating an eddy current in said disc.

8. A rowing machine in accordance with claim 3, further including support members for rotatably mounting said pair of oars on said frame respectively,
each of said support members including a disc rotated interlockingly with the corresponding one of said oars,
each of said angular velocity detecting means including an optical sensor for optically detecting the angle of rotation of said disc.

9. A rowing machine in accordance with claim 1, wherein
said control means includes means for operating the travel speed on the basis of angular velocity values detected by said angular velocity detecting means to make said display means display said operated travel speed.

10. A rowing machine in accordance with claim 1, wherein
said control means includes means for operating the travel distance on the basis of angular velocity values detected by said angular velocity detecting means to make said display means display said operated travel distance.

11. A rowing machine in accordance with claim 1, wherein
said display means includes CRT display means.

* * * * *